United States Patent
Chopdekar et al.

(10) Patent No.: US 6,670,370 B1
(45) Date of Patent: Dec. 30, 2003

(54) DEXTROMETHORPHAN TANNATE

(75) Inventors: Vilas M. Chopdekar, Edison, NJ (US); James R. Schleck, Somerset, NJ (US); Hemant S. Desai, Flemington, NJ (US)

(73) Assignee: Jame Fine Chemicals, Inc., Bound Brook, NJ (US)

( * ) Notice: Subject to any disclaimer, the term of this patent is extended or adjusted under 35 U.S.C. 154(b) by 45 days.

(21) Appl. No.: 10/281,725

(22) Filed: Oct. 28, 2002

Related U.S. Application Data

(63) Continuation-in-part of application No. 10/017,130, filed on Dec. 14, 2001.

(51) Int. Cl.$^7$ .............. A61K 31/485; C07C 69/88; C07D 22/28
(52) U.S. Cl. .......... 514/289; 514/850; 514/855; 514/326; 560/68; 546/74
(58) Field of Search ............... 514/289, 326, 514/850, 855; 560/68; 546/74

(56) References Cited

U.S. PATENT DOCUMENTS

| | | | |
|---|---|---|---|
| 3,282,789 A | 11/1966 | Marty et al. ............... 167/82 |
| 5,599,846 A | 2/1997 | Chopdekar et al. ......... 514/653 |
| 5,663,415 A | 9/1997 | Chopdekar et al. ........... 560/68 |
| 6,037,358 A | 3/2000 | Gordziel ..................... 514/357 |
| 6,287,597 B1 | 9/2001 | Gordziel ..................... 424/464 |
| 6,306,904 B1 | 10/2001 | Gordziel ..................... 514/530 |
| 6,509,492 B1 * | 1/2003 | Venkataraman |

FOREIGN PATENT DOCUMENTS

| | | | |
|---|---|---|---|
| JP | 54034814 | 4/1974 | |
| JP | 54034814 B4 * | 10/1979 | |
| WO | WO 02/05745 A2 | 1/2002 | |
| WO | WO 02/05746 A3 | 1/2002 | C07C/69/88 |
| WO | WO 02/05747 A2 | 1/2002 | |

OTHER PUBLICATIONS

Sawai et al., JP –54034814 B4 (English Translation).*
Sawai et al., HCAPLUS Copyright 2002 ACS, Accession #: 1980:135443; Abstract of JP 54034814 B4.*

* cited by examiner

Primary Examiner—Samuel Barts
Assistant Examiner—Michael C. Henry
(74) Attorney, Agent, or Firm—Jack Matalon

(57) ABSTRACT

The invention pertains to a composition comprising dextromethorphan tannate and to a method for preparing dextromethorphan tannate by reacting dextromethorphan at a temperature of about 80 to about 180° C. with tannic acid either neat or as an aqueous slurry containing about 5 to about 30 wt. % water. The dextromethorphan tannate has extended release properties and is useful in pharmaceutical compositions as an antitussive for human beings.

46 Claims, No Drawings

DEXTROMETHORPHAN TANNATE

CROSS-REFERENCE TO RELATED APPLICATION

This application is a continuation-in-part of application Ser. No. 10/017,130 filed Dec. 14, 2001.

FIELD OF THE INVENTION

The invention pertains to dextromethorphan tannate, its method of preparation and to pharmaceutical compositions containing dextromethorphan tannate.

BACKGROUND OF THE INVENTION

Dextromethorphan (hereinafter also referred to as dextromethorphan free base) is a well-known commercially available compound. It is the methyl ether of the dextrorotary isomer of levorphanol, anarcotic analgesic. Its chemical name is 3-methoxy-17-methyl-9α, 13α, 14α-morphinan and its CAS number is 125-71-3. It is a solid having a melting point of 109.5 to 112.5° C. and its molecular formula is $C_{18}H_{25}NO$. It is insoluble in water, and therefore is utilized typically in the form of its hydrobromide monohydrate salt that is soluble in water.

Dextromethorphan finds its principal use as an antitussive, i.e., a cough suppressant that acts centrally to elevate the threshold for coughing, but it does not have addictive, analgesic or sedative actions and does not produce respiratory depression with usual doses. It is typically administered to human beings in need of such medication in the form of tablets and/or suspensions. It frequently is administered as an antitussive/expectorant composition consisting of dextromethorphan hydrobromide monohydrate and guaifenesin.

In contradistinction to the antihistamines, which are unstable in the form of their free bases, dextromethorphan is relatively stable. Therefore, little, if any attention, has been paid in recent years to improving dextromethorphan compositions. On the other hand, there is a considerable amount of prior art which has emerged in recent years directed to salts of antihistamines, principally tannate salts. For example, see U.S. Pat. Nos. 5,599,846; 5,663,415; 6,037,358; 6,287,597; and 6,306,904.

U.S. Pat. No. 3,282,789 is directed to stable liquid colloidal tannate compositions. Examples 1–6 of this patent disclose formulations containing dextromethorphan tannate. However, no mention is made in the '789 patent as to the physical properties of the dextromethorphan tannate employed in the formulations nor is there any disclosure as to the method by which the dextromethorphan tannate was prepared. The patentees allude to several related patents involving the preparation of tannates of other materials by reacting a material with tannic acid in the presence of isopropyl alcohol employed as a solvent in the reaction mixture (such preparatory method is hereinafter referred to as the "IPA route"). Furthermore, the state of the art at the time of this patent was that tannates were always prepared by the IPA route. Such state of the art is also disclosed in one or more of the five U.S. patents identified above. Therefore, it is reasonable to assume that the dextromethorphan tannate employed in the examples of the '789 patent was prepared using the IPA route.

Tannic acid is commercially available and is used in many industrial applications. It is frequently referred to as gallotannic acid, gallotannin; glycerite or tannin. It is a pale tan powder having a decomposition point of 210–215° C., and is highly soluble in water and alcohols. Its molecular formula is $C_{76}H_{52}O_{46}$; its CAS number is 1401-55-4. Tannic acid is typically produced from Turkish or Chinese nutgall and has a complex non-uniform chemistry and typically contains about 5–10 wt. % water.

Dextromethorphan is quite stable and therefore would not require the addition of a material such as tannic acid to render it stable. Due to its water insolubility, dextromethorphan must, however, be utilized in the form of a salt, typically the hydrobromide monohydrate salt (hereinafter referred to as "dextromethorphan hydrobromide" or "dextromethorphan-HBr"). However, dextromethorphan hydro-bromide does have a drawback: it is readily absorbed in the patient's body, but its action is relatively short-lived. Accordingly, while it provides relatively quick cough suppression relief to the patient, the patient is required to take relatively high doses several times a day until the condition which necessitated the administration of the dextromethorphan hydrobronide has been alleviated.

It would be very desirable if a form of dextromethorphan was available which would have extended-release properties, i.e., the dextromethorphan would be slowly released into the patient's bloodstream over a prolonged period of time. Thus far, the only slow-release forms of dextromethorphan, which are available, are those such as polymer-coated tablets. Such prior art formulations provide mixed results in that the dextromethorphan is not available for adsorption into the patient's bloodstream until the polymeric coating has been dissolved, but thereafter the dextromethorphan is quickly absorbed and metabolized. The result is that frequently, the dextromethorphan hydrobromide must again be administered to the patient within the period of only a few hours.

DETAILED DESCRIPTION OF THE INVENTION

It has now been found that it is possible to provide an extended-release form of dextromethorphan by reacting it with tannic acid so as to form dextromethorphan tannate, which differs dramatically from commercially available dextromethorphan tannate, or dextromethorphan tannate synthesized using the IPA route.

The dextromethorphan tannate of the invention may be readily prepared by the following method:

Dextromethorphan free base is obtained from a commercial source or a commercially available dextromethorphan acid salt such as dextromethorphan hydrobromide is treated with an aqueous base, e.g., 10% sodium hydroxide, to release the free base which is then washed to remove any sodium salts contained therein.

Tannic acid is heated to a temperature in the range of about 80 to about 180° C., preferably 110 to 150° C., and the dextromethorphan free base is slowly added, while mixing, to the heated tannic acid slurry over a period of a few minutes to about one hour. Since the reaction mixture becomes very viscous and difficult to stir as the reaction proceeds, it is desirable to add about 5 to about 30%, preferably 5 to 15 wt. %, additional water before adding the dextromethorphan free base. The reaction mixture is continued to be stirred while maintaining such temperature range for a period of about 10 minutes to about 2 hours. Thereafter, the reaction mixture is cooled to room temperature. The resultant solid reaction mass comprising the dextromethorphan tannate is preferably thereafter milled to form a free-flowing powder preferably to a particle size of about 50 to about 200 mesh Since the dextromethorphan tannate product as prepared is moist, it may be dried to a moisture content of 5 wt. % or less by conventional methods, e.g., heat lamp, in a steam of air or nitrogen, vacuum drying, etc. at a temperature of about 20 to about 80° C. for about 30 minutes to about 24 hours. However, the moisture content is relatively irrelevant in respect to its usage as a cough suppressant since the dextromethorphan tannate of the invention is intended to be ingested.

The molar ratio of the dextromethorphan free base to the tannic acid is generally in the range of about 4 to about 8, preferably 5–6, moles of dextromethorphan per mole of tannic acid.

The dextromethorphan tannate of the invention has the following physical properties: It has a softening point in the range of about 140° C. when the product has a moisture content of about 3% and a softening point of about 100° C. when the product has a moisture content of about 5% (the softening point is inversely related to the moisture content of the product). By contrast, commercially available dextromethorphan tannate has a softening point of about 174° C. with a moisture content of about 5%, while dextromethorphan tannate synthesized via the IPA route has a softening point of about 172° C. with a moisture content of about 5%. The dextromethorphan tannate of the invention is a tan-colored powder that is slightly soluble in water. The dextromethorphan free base is a white powder that is insoluble in water, while tannic acid is a tan powder that is soluble in water.

The dextromethorphan tannate of the invention in the form of particles having a particle size of about 100 mesh has a tap density in the range of about 0.7 to about 0.85 g/cc, while both commercial available dextromethorphan tannate and dextromethorphan tannate synthesized via the IPA route in the form of particles having the same mesh size have a tap density of about 0.4 g/cc, or lower.

A further and very important distinction between the dextromethorphan tannate composition of the invention relates to its purity level. Commercially available dextro methorphan tannate as well as dextromethorphan tannate synthesized using the IPA route contain relatively high levels of unreacted dextromethorphan free base, i.e., in the order of 2.5–6 wt. % (based on the weight of the dextromethorphan tannate) of unreacted dextromethorphan free base. In contradistinction thereto, the dextro methorphan tannate of the invention contains substantially no unreacted dextromethorphan free base, i.e., the amount of such unreacted dextromethorphan free base in the dextromethorphan tannate composition of the invention will be less than 2 wt. %, typically less than 1 wt. % and often less than 0.5 wt. %.

Further distinctions between the dextromethorphan tannate of the invention and dextromethorphan tannate synthesized via the IPA route may be found by comparing the spectra obtained by FTIR analysis as shown in Example 8 below.

The dextromethorphan tannate of the invention may be prepared for oral administration in the form of pharmaceutically acceptable compositions such as powders, capsules, elixirs, syrups, etc. Preferably, the compositions are prepared in the form of tablets containing about 10 to about 100 mg of dextromethorphan tannate per tablet or as a suspension, i.e., a liquid, wherein each 5 ml (teaspoon) of liquid would contain about 5 to about 60 mg of the dextromethorphan tannate.

Tablets containing the unique dextromethorphan tannate of the invention may be prepared in a conventional manner by the addition of suitable pharmaceutical carriers, including fillers, diluents, lubricants and the like as well as conventional and well known binding and disintegrating agents. A typical tablet composition of the present invention will contain, in addition to the dextromethorphan tannate, microcrystaltine cellulose, corn starch, magnesium stearate, croscarmellose sodium and coloring matter.

The suspension formulations of the dextromethorphan tannate of the present invention will typically additionally contain citric acid, caramel, glycerin, sorbitol solution, propylene glycol, saccharin sodium, sodium benzoate, flavoring agent and purified water.

If desired, the dextromethorphan tannate of the invention may be formulated with other pharmaceutically active ingredients such as antihistamines and antitussives, e.g., chlorpheniramine, dexchlorpheniramine, brompheniine, dexbrompheniramine, pyrilamine, phenylephrine, ephedrine, pseudoephedrine, carbetapentane, carbinoxamie, guaifenesin, and the like. Typically, these other active ingredients will be employed in the form of their free bases or as their salts, e.g., citrates, maleates, hydrobromides, hydrochlorides, tannates, etc. Of course, the dosage of the dextromethorphan tannate of the present invention, alone or in combination with other pharmaceutically active ingredients to be administered, will be dependent on the age, health and weight of the recipient, types of concurrent treatment, if any, frequency of treatment and effect desired.

The following nonlimiting examples shall serve to illustrate the present invention. Unless otherwise indicated, all parts and percentages are on a weight basis.

EXAMPLE 1

A 500 ml flask was equipped with a stirrer, thermometer, nitrogen blanket and a hot water bath. The hot water bath was heated to, and maintained at, a temperature of 85 to 100° C. Water in the amount of 25 g was placed in the flask and thereafter 88.8 g(0.052 m) of tannic acid were added to the heated water over a period of about 5 minutes. Stirring was continued for an additional 10 minutes, while maintaining a temperature of 85–100° C. to thereby obtain a smooth slurry of the tannic acid. Thereafter, 71.2 g (0.262 m) of dextromethorphan were added to the heated slurry, with stirring, over a period of about 15 minutes, while maintaining a temperature of 85–100° C. String was continued for a period of about 1 hour, while maintaining the same temperature and the reaction mixture was then allowed to cool to room temperature. The product became very hard after about 2 hours at room temperature. The yield of the product obtained was 148.8 g (95.6% of theory). Karl Fischer analysis indicated that the product contained 11.1% water. The product was milled to a fine powder and thereafter dried to a moisture content of 3.6% (K.F.) at a temperature of about 40–45° C. while sparging with nitrogen over a 24 hour period. The dried product had a softening point of about 108–115° C.

EXAMPLE 2

A 500 cc resin flask was fitted with a stirrer, thermometer, nitrogen blanket and a hot oil bath. Dextromethorphan in the amount of 71.2 g (0.262 m) was placed in the flask and the temperature of the oil bath was gradually raised to 140–150° C. At this point, the dextromethorphan (which melts at about 110° C.) was fully molten. Tannic acid (neat) in the amount of 89 g (0.052 m) was added over a period of several minutes to the molten dextromethorphan, while stirring was continued and the oil bath temperature was maintained at 140–150° C. Thereafter, stirring was continued for about 2 hours, while maintaining the temperature of the oil bath at about 140–150° C. The reaction mixture was then cooled to room temperature and the tan-colored product was milled to a fine powder, which was then dried under 29 inches of vacuum at 50–55° C. for 24 hours. The yield of the product was 151 g (97% of theory). The softening point of the product which had a moisture content of 2.8% (K.F.) was 138–143° C.

EXAMPLE 3

Examples 1 and 2 were repeated and the resultant dextromethorphan tannate product was dried to various moisture levels. The softening points of the dextromethorphan tannate product at these moisture levels were determined to be as follows:

| % Moisture (K.F.) | Softening Point ° C. |
|---|---|
| 14.9 | 32–45 |
| 9.5 | 50–55 |
| 8.3 | 56–62 |
| 7.7 | 65–72 |
| 7.2 | 70–77 |
| 6.97 | 82–90 |
| 5.00 | 97–104 |
| 3.8 | 100–107 |
| 3.6 | 108–115 |
| 2.8 | 140–143 |

EXAMPLE 4

The softening point of a commercially available sample of dextromethorphan tannate having a moisture content (K.F.) of 4.95% was found to be 170–177° C. in contrast to the softening point of 98 to 105° C. for the dextromethorphan tannate of the invention having the same moisture content. The dramatic difference in such softening points clearly indicates that the dextromethorphan tannate of the invention is different from that of the commercially available dextromethorphan tannate.

EXAMPLE 5

Example 1 was repeated using the following materials: 34.02 g of tannic acid and 340 g of isopropyl alcohol were placed in the reaction vessel and stirred while maintaining a temperature of about 40–45° C. Thereafter, a clear solution of 27.1 g of dextromethorphan free base in 270 g of isopropyl alcohol was added, over a period of one hour, while stirring, to the reaction vessel while the temperature of the reaction mixture was raised to, and maintained at, 45–50° for an additional hour. The resultant cream-colored solid was filtered off and washed with 25 g of isopropyl alcohol. The reaction product was then dried under vacuum at a temperature of 55–65° C. The yield of the product was 51.1 g (83.6% of theory). The dried product had a moisture content of 4.95% had a softening point of 172–177° C.

EXAMPLE 6

Comparisons were made in the tap density of the dextromethorphan tannate product of the invention made in accordance with the hot melt procedure as exemplified by Examples 1 and 2 versus the tap density of a commercially available dextro-methorphan tannate product and the tap density of a dextromethorphan tannate product made via the IPA route as exemplified by Example 5. Each dextromethorphan tannate product was dried to a moisture level (K.F.) of 5% and milled to form a free-flowing powder having a particle size of about 100 mesh. The tap densities of the three dextromethorphan tannate products were found to be as follows:

| D-M Tannate of the invention, Tap Density, g/cc | Commercially available D-M Tannate, Tap Density, g/cc | D-M Tannate synthesized by IPA route (Example 5), Tap Density, g/cc |
|---|---|---|
| 0.723 | 0.313 | 0.321 |

The very large difference in tap densities between the dextromethorphan product of the invention and the commercially available dextromethorphan tannate product and the dextromethorphan tannate product synthesized by the IPA route is again conclusive evidence that the dextromethorphan tannate product of the invention is uniquely different from the prior art dextromethorphan tannate products.

EXAMPLE 7

Comparisons were made in the percentages of unreacted dextromethorphan free base in samples of the dextromethorphan tannate product of the invention made in accordance with the hot melt procedure as exemplified by Examples 1, a commercially available dextromethorphan tannate product and the dextromethorphan tannate product made via the IPA route as exemplified by Example 5. Each sample was dried to a moisture level (K.F.) of 5% and milled to form a free-flowing powder having a particle size of 100 mesh The percentage of unreacted dextromethorphan free base in each type of product was determined by mixing 1 g samples of each type of product with 110 ml of methylene chloride for about 10 minutes, filtering off the methylene chloride extract and thereafter titrating the methylene chloride extract by the typical method involving the use of an acetic acid solution of perchloric acid with crystal violet as the indicator. The percentages were found to be as follows:

| D-M Tannate of the invention, Unreacted D-M, % | Commercially available D-M Tannate, Unreacted D-M, % | D-M Tannate synthesized by IPA route (Example 5), Unreacted D-M, % |
|---|---|---|
| 0.2 | 2.5 | 5.6 |

The very low level of unreacted dextromethorphan base in the dextromethorphan tannate of the invention is not only indicative of its extremely high purity, but also provides further evidence that the dextromethorphan tannate of the invention is uniquely different from the commercially available dextromethorphan tannate as well as dextromethorphan tannate synthesized by the IPA route.

EXAMPLE 8

The dextromethorphan tannate of the invention prepared by the hot melt procedure as exemplified by Example 1 and dextromethorphan tannate prepared by the IPA route as exemplified by Example 5 were subjected to FTI analysis. The spectral differences as shown below clearly indicate that the dextromethorphan product of the invention is uniquely different from the prior art dextromethorphan tannate:

| Spectral Line, 1/cm | D-M Tannate of the Invention | D-M Tannate synthesized by IPA route (Example 5) |
| --- | --- | --- |
| 2950 | Very slight depression | Small depression |
| 2900 | — | Very slight depression |
| 1725 | Moderate depression | Moderate depression |
| 1625 | Moderate depression | Moderate depression |
| 1350 | Moderate depression | Very long depression |
| 1200 | Long depression | Very long depression |
| 1050 | Moderate depression | Very long depression |
| 800 | Small depression | Moderate depression |
| 625 | Long, narrow depression | — |
| 600 | Long, narrow depression | — |

EXAMPLE 9

Sawai et al. disclose in JP 54034814 the mixing dextromethorphan-HBr with tannic acid (along with other ingredients such as Na casein, lactose and potato starch) to arrive at a mixture which will mask the bitter taste of dextromethorphan-HBr. The mixture prepared by Sawai et al. could not possibly have resulted in the formation of dextromethorphan tannate since tannic acid is a weaker acid than HBr and, in accordance with the accepted principles of acid/base chemistry, tannic acid could not have possibly replaced hydrogen bromide so as to form dextromethorphan tanned. In order to demonstrate that Sawai et al. could not possibly have prepared dextromethorphan tannate, the work reported by Sawai et al. was repeated and the physical properties of the product prepared by Sawai et al. were compared with the physical properties of dextromethorphan tannate of the invention.

Experiment "A"

14 g of dextromethorphan HBr was mixed with 12 g of water and 34 g of tannic acid. The reaction mixture was heated to 90° C. and stirred for several minutes. After cooling to room temperature, a portion of the product was dried at 50±5° C. under 29.5 inches vacuum for 4 hours. One gram of the dried product was added to 110 g of methylene chloride and the mixture was stirred for 20 minutes at room temperature. The resultant mixture was filtered and the precipitate was dried. The precipitate (about 30 g) had a decomposition point of about 210° C. Such decomposition point compares quite closely to the reference decomposition point of 210–215° C. for pure tannic acid, which indicated that the tannic acid had not reacted with the dextromethorphan HBr.

The filtrate was evaporated to dryness and the resultant solid (about 12 g) was then dried. The dried solid had a melting point of about 121° C. which compared quite closely to the melting point of 123° C. for pure dextromethorphan-HBr which indicated that the tannic acid had not reacted with the dextromethorphan-HBr. A sample of the dried solid was then subject to FTIR analysis and the spectrum which was obtained was then compared to the FTIR spectrum of pure dextromethorphan HBR. The two spectra were nearly identical. Therefore, it is clear that the dextromethorphan-HBr did not react with the tannic acid to form dextromethorphan tannate and that the dextromethorphan-HBr was present as a mixture with the tannic acid.

Experiment "B"

Experiment "A" was repeated using additional amounts of lactose, potato starch and Na casein as described by Sawai et al. One gram of the reaction product was mixed with 110 g methylene chloride and then filtered. The solid obtained by evaporating the methylene chloride filtrate to dryness was again found by melting point and FTIR analysis to be substantially all unreacted dextromethorphan-HBr, while the precipitate which did not dissolve in the methylene chloride was found to be a mixture of tannic acid, lactose, potato starch and Na casein. Therefore, it is clear that despite the presence of lactose, potato starch and casein, the dextromethorphan-HBR did not react with the tannic acid and that the reaction product consisted of a mixture of dextromethorphan-HBr, tannic acid, lactose, potato starch and Na casein.

Experiment "C"

14 g of dextromethorphan free base was mixed with 12 g of water and 36 g of tannate acid. The mixture was heated with stirring, to 90° C. and maintained at such temperature for several minutes. After cooling to room temperature, the reaction product was dried and powdered. A sample of the powdered product was mixed with methylene chloride, but no dissolution occurred, indicating that the reaction product did not consist of dextromethorphan free base. A sample of the reaction product was dried to a moisture (K.F.) level of about 4% and it was determined that such material had a softening point of about 100° C. (in comparison to the sharp melting point of 123° C. for dextromethorphan-HBr, the melting point of 109.5–112.5° C. for dextromethorphan free base and the decomposition point of 210–215° C. for tannic acid). The reaction product was also subjected to FTIR analysis and the spectrum obtained thereby was quite different from that of either dextromethorphan free base or tannic acid (or dextromethorphan-HBr). Therefore, it is clear that when dextromethorphan free base is reacted with tannic acid in accordance with the process of the invention, a unique type of dextromethorphan tannate product is obtained.

What is claimed is:

1. A composition comprising dextromethorphan tannate having a softening point from about 140–143° C. to about 97–104° C. when the dextromethorphan tannate has a corresponding moisture content ranging from about 2.8% to about 5.0%.

2. A therapeutic antitussive composition comprising a pharmaceutically effective amount of the composition of claim 1.

3. A therapeutic antitussive composition as claimed in claim 2 in tablet form.

4. A therapeutic antitussive composition as claimed in claim 2 in suspension form.

5. A therapeutic antitussive composition as claimed in claim 2 further comprising one or more expectorant and/or antihistamine compositions.

6. The composition of claim 5 wherein the expectorant and/or antihistamine compositions are selected from the group consisting of guaifenesin, chlorpheniramine, brompheniramine, pyrilamine, phenylephrine, ephedrine, pseudoephedrine, carbeta-pentane and carbinoxamine.

7. A method for suppressing coughing in a human being which comprises orally administering to such human being in need of cough suppression a therapeutic amount of the composition of claim 1.

8. A method as claimed in claim 7 wherein said composition is in tablet form.

9. A method as claimed in claim 7 wherein said composition is in suspension form.

10. A composition comprising dextromethorphan tannate having a tap density of about 0.7 to about 0.85 g/cc.

11. A therapeutic antitussive composition comprising a pharmaceutically effective amount of the composition of claim 10.

12. A therapeutic antitussive composition as claimed in claim 11 in tablet form.

13. A therapeutic antitussive composition as claimed in claim 11 in suspension form.

14. A therapeutic antitussive composition as claimed in claim 11 further comprising one or more expectorant and/or antihistamine compositions.

15. The composition of claim 14 wherein the expectorant and/or antihistamine compositions are selected from the group consisting of guaifenesin, chlorpheniramine, brompheniramine, pyrilamine, phenylephrine, ephedrine, pseudoephedrine, carbeta-pentane and carbinoxamine.

16. A method for suppressing coughing in a human being which comprises orally administering to such human being in need of cough suppression a therapeutic amount of the composition of claim 10.

17. A method as claimed in claim 16 wherein said composition is in tablet form.

18. A method as claimed in claim 16 wherein said composition is in suspension form.

19. A composition comprising dextromethorphan tannate containing substantially no unreacted dextromethorphan.

20. The composition of claim 19 wherein the amount of any unreacted dextromethorphan present in the composition is less than about 2 wt. %, based on the weight of the dextromethorphan tannate.

21. The composition of claim 20 wherein the amount of any unreacted dextromethorphan present in the composition is less than about 1 wt %, based on the weight of the dextromethorphan tannate.

22. The composition of claim 21 wherein the amount of any unreacted dextromethorphan present in the composition is less than about 0.5 wt. %, based on the weight of the dextromethorphan tannate.

23. A therapeutic antitussive composition comprising a pharmaceutically effective amount of the composition of claim 20.

24. A therapeutic antitussive composition as claimed in claim 23 in tablet form.

25. A therapeutic composition as claimed in claim 23 in suspension form.

26. A therapeutic antitussive composition as claimed in claim 23 further comprising one or more expectorant and/or antihistamine compositions.

27. The composition of claim 26 wherein the expectorant and/or antihistamine compositions are selected from the group consisting of guaifenesin, chlorpheniramine, brompheniramine, pyrilamine, phenylephrine, ephedrine, pseudoephedrine, carbeta-pentane and carbinoxamine.

28. A method for suppressing coughing in a human being which comprises orally administering to such human being in need of cough suppression a therapeutic amount of the composition of claim 20.

29. A method as claimed in claim 28 wherein said composition is in tablet form.

30. A method as claimed in claim 28 wherein said composition is in suspension form.

31. A composition of matter comprising dextromethorphan tannate having the following FTIR spectral analysis:

| Spectral Line, 1/cm | Observation |
| --- | --- |
| about 2950 | Very slight depression |
| about 2900 | Flat |
| about 1725 | Moderate depression |
| about 1625 | Moderate depression |
| about 1350 | Moderate depression |
| about 1200 | Long depression |
| about 1050 | Moderate depression |
| about 800 | Small depression |
| about 625 | Long, narrow depression |
| about 600 | Long, narrow depression |

32. A therapeutic antitussive composition comprising a pharmaceutically effective amount of the composition of claim 31.

33. A therapeutic antitussive composition as claimed in claim 32 in tablet form.

34. A therapeutic composition as claimed in claim 32 in suspension form.

35. A therapeutic antitussive composition as claimed in claim 32 further comprising one or more expectorant and/or antihistamine compositions.

36. The composition of claim 35 wherein the expectorant and/or antihistamine compositions are selected from the group consisting of guaifenesin, chlorpheniramine, brompheniramine, pyrilamine, phenylephrine, ephedrine, pseudoephedrine, carbeta-pentane and carbinoxamine.

37. A method for suppressing coughing in a human being which comprises orally administering to such human being in need of cough suppression a therapeutic amount of the composition of claim 30.

38. A method as claimed in claim 37 wherein said composition is in tablet form.

39. A method as claimed in claim 38 wherein said composition is in suspension form.

40. A method for preparing dextromethorphan tannate which comprises mixing dextromethorphan free base with tannic acid in the presence of 0 to about 30 wt. % water at a temperature of about 80 to about 180° C. and thereafter recovering the resultant dextromethorphan tannate.

41. The method of claim 40 wherein the dextromethorphan is heated to a temperature of 110 to 150° C. and water is present in the amount of 5 to 15 wt. %.

42. The method of claim 40 wherein the resultant dextromethorphan tannate is dried to a moisture content of about 5 wt. % or less.

43. The method of claim 40 wherein the dextromethorphan free base is employed in an amount of about 4 to about 8 moles of dextromethorphan per mole of tannic acid.

44. The method of claim 43 wherein the dextromethorphan is employed in an amount of 5 to 6 moles of dextromethorphan per mole of tannic acid.

45. The method of claim 40 wherein the resultant dextromethorphan tannate is milled to provide a free-flowing powder.

46. The method of claim 45 wherein the powder has a particle size in the range of about 50 to about 200 mesh.

* * * * *